(12) United States Patent
Settles

(10) Patent No.: US 8,113,069 B2
(45) Date of Patent: Feb. 14, 2012

(54) AERODYNAMIC SAMPLER FOR CHEMICAL/BIOLOGICAL TRACE DETECTION

(75) Inventor: Gary S. Settles, Bellefonte, PA (US)

(73) Assignee: The Penn State Research Foundation, University Park, PA (US)

( * ) Notice: Subject to any disclaimer, the term of this patent is extended or adjusted under 35 U.S.C. 154(b) by 478 days.

(21) Appl. No.: 12/140,660

(22) Filed: Jun. 17, 2008

(65) Prior Publication Data

US 2008/0314166 A1 Dec. 25, 2008

Related U.S. Application Data

(60) Provisional application No. 60/944,923, filed on Jun. 19, 2007.

(51) Int. Cl.
*G01N 1/10* (2006.01)
(52) U.S. Cl. ............. 73/864.35; 73/863; 73/864.31; 73/864.33
(58) Field of Classification Search ............. 73/864.35, 73/863, 864, 864.31, 864.33, 864.34, 864.53, 73/864.54

See application file for complete search history.

(56) References Cited

U.S. PATENT DOCUMENTS

| | | | | |
|---|---|---|---|---|
| 4,057,396 A | * | 11/1977 | Matovich | 422/202 |
| 4,234,543 A | * | 11/1980 | Matovich | 422/109 |
| 4,754,638 A | * | 7/1988 | Brayman et al. | 73/40.7 |
| 4,813,268 A | * | 3/1989 | Helvey | 73/40.7 |
| 4,909,090 A | | 3/1990 | McGown et al. | |
| 5,123,274 A | | 6/1992 | Carroll et al. | |
| 5,942,699 A | | 8/1999 | Ornath et al. | |
| 5,998,215 A | * | 12/1999 | Prather et al. | 436/173 |
| 6,828,795 B2 | * | 12/2004 | Krasnobaev et al. | 324/464 |
| 2003/0155506 A1 | | 8/2003 | Motchkine et al. | |

OTHER PUBLICATIONS

Settles, Gary S et al.; Aerodynamic Sampling for Landmine Trace Detection; SPIE Aerosense 4394, paper 108; Apr. 2001.
Smedley, G.T. Entrainment of Fine Particles from Surfaces by Gas Jets Impinging at Normal Incidence; Experiments in Fluids; Mar. 1999.
Gary S. Settles; Sniffers; Fluid-Dynamic Sampling for Olfactory Trace Detection in Nature and Homeland Security—The 2004 Freeman Scholar Lecture; Journal of Fluids Engineering; vol. 127; pp. 189-218; Mar. 2005.
Thomas Rueegg, Ph.D. et al.; Local Capture of Contaminants; ASHRAE Journal; vol. 46; Jan. 2004; pp. 26-29.

* cited by examiner

*Primary Examiner* — Hezron E Williams
*Assistant Examiner* — Rodney T Frank
(74) *Attorney, Agent, or Firm* — Gifford, Krass, Sprinkle, Anderson & Citkowski, P.C.

(57) ABSTRACT

An aerodynamic sampler for sampling particles from a surface or a flowing gas stream is provided. The sampler can include an arcuate-shaped shroud having a first opening and a second opening, the first opening being directed in a first direction and the second opening oppositely disposed and spaced apart from the first opening. A gas nozzle having at least one gas outlet directed generally in the first direction can be included and may or may not be located at least partially within the shroud. The gas nozzle is operable to supply a gas jet to a surface that is proximate the first opening of the shroud. In addition, a suction device operable to pull or suck the gas proximate the first opening through the second opening and afford for the gas to enter a detector is provided. The arcuate-shaped shroud can be a bell-shaped shroud with the first opening located at a bottom of the bell-shape.

12 Claims, 5 Drawing Sheets

AERODYNAMIC SAMPLER FOR CHEMICAL/BIOLOGICAL TRACE DETECTION

CROSS-REFERENCE TO RELATED APPLICATIONS

This application claims priority to U.S. Provisional Patent Application Ser. No. 60/944,923 filed on Jun. 19, 2007, which is incorporated herein by reference in its entirety.

FIELD OF THE INVENTION

The present invention relates generally to devices for obtaining samples for analysis and more particularly to an aerodynamic sampler for chemical and/or biological trace detection.

BACKGROUND OF THE INVENTION

Modern chemical detectors, such as artificial (electronic) noses, ion-mobility spectrometers, gas chromatographs and the like, have evolved such that miniaturized and hand-held, briefcase-sized-or-smaller chemical trace detectors are now available. If chemical signals are thoroughly dispersed in the atmosphere (e.g. nitrogen compounds in city smog), the application of a small suction at a device inlet can be sufficient to bring chemical traces to bear upon the sensor, thus affording the possibility of a detection step. However, many other cases exist where aerodynamic sampling is required before detection can occur. Canines, for example, are natural chemical trace detectors with a built-in aerodynamic sampler, the slit canine nostril [1], that is positioned in proximity to a trace chemical source with sampling and subsequent detection occurring, or that samples chemical plumes carried by the natural wind. Similarly, an active, air-moving sampler is required to "reach out" from a manmade hand-held or otherwise mobile detector in order to acquire vapor and/or particulate traces from surfaces being sampled.

There has been a variety of attempts to provide aerodynamic samplers. The potential-flow suction inlet is well known in fluid dynamics with the application of that science to heating, ventilation and air conditioning documented in many textbooks, e.g. [2]. The potential-flow suction inlet can take on several forms such as a blank tube, flanged tube, bellmouth inlet, etc. However, the "reach" of the potential-flow suction inlet is severely limited by the nature of potential flow. To overcome this limitation, scenting animals have developed long noses and the mobility to position them in close proximity to a scent source [1].

Another approach to aerodynamic sampling uses an intake vortex. Helmholtz's vortex laws reveal that a line vortex cannot end in free air, but it can attach to a solid surface. For example, jet engines can "suck up" rubble from runways through vortex impingement [3] and a tornado represents a vortex tube that attaches to the ground and extends powerful suction due to the low pressure in the vortex core. The vortex concept has been disclosed in relation to a sampling device with a small tornado-like swirling flow that may "reach out" to a surface and convey vapor/particulate traces from the surface to a sensor element of a trace detector [4]. The upward axial flow along the vortex core transports a trace sample to the inlet of the device, where suction applied to a small central tube captures some of the trace-bearing airstream. Thereafter, the trace-bearing airstream can be interrogated for chemical content by a suitable trace detector such as an ion mobility spectrometer (IMS).

SUMMARY OF THE INVENTION

An aerodynamic sampler for sampling particles from a surface or a flowing gas stream is provided. The sampler can include an arcuate-shaped shroud having a first opening and a second opening, the first opening being directed in a first direction and the second opening oppositely disposed and spaced apart from the first opening. A gas nozzle having at least one gas outlet directed generally in the first direction can be included and may or may not be located at least partially within the shroud. The gas nozzle is operable to supply a jet of gas to a surface that is proximate the first opening of the shroud. In addition, a suction device operable to pull or suck or otherwise induce a flow of the gas proximate the first opening through the second opening and afford for the gas to enter a detector is provided. The arcuate-shaped shroud can be a bell-shaped shroud with the first opening located at a bottom of the bell-shape.

In some instances, the suction device is provided by a fan or blower, while in other instances the suction device is provided by a second gas nozzle that provides a flow of gas in the second direction. Other gas movers may be used, e.g. a positive-displacement pump.

DETAILED DESCRIPTION OF THE PREFERRED EMBODIMENTS

Research experience at the Penn State University Gas Dynamics Laboratory and elsewhere has demonstrated that trace contaminants are effectively dislodged from a surface (e.g. from people's clothing) by a brief turbulent jet impact [8, 9]. It is known to those in the art that shear stress generated by the jet impact in a direction parallel to the surface being sampled is active in detaching trace-bearing particles from that surface. It is also known that the jet impact "rolls out" along the impacted surface in a "starting vortex" [10] and forms a "wall jet" that can be made to separate from the impacted surface. Capturing the wall jet by suction through an appropriately designed "shroud" can thus afford for a particulate and/or a vapor signal dislodged from the surface to be examined. Such an airborne sampling process can be quite brief (e.g. milliseconds) such that a volume of air sampled is small and can avoid the need for undue pre-concentration. It is thus possible to interrogate the volume of air sampled directly, e.g. using an ion mobility spectrometer (IMS) detector, with appropriate concern for the desorption of trace chemicals from any particles that are captured.

Figure 1:
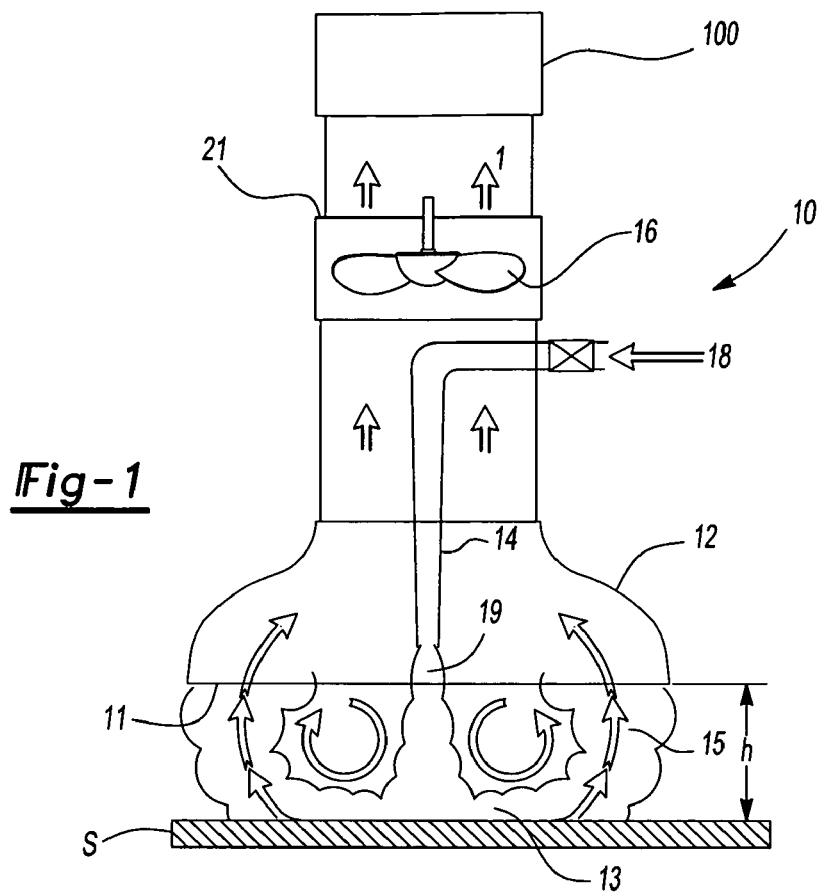
FIG. 1 is a side view of a first embodiment of an aerodynamic sampler according to the present invention.
Figure 2:
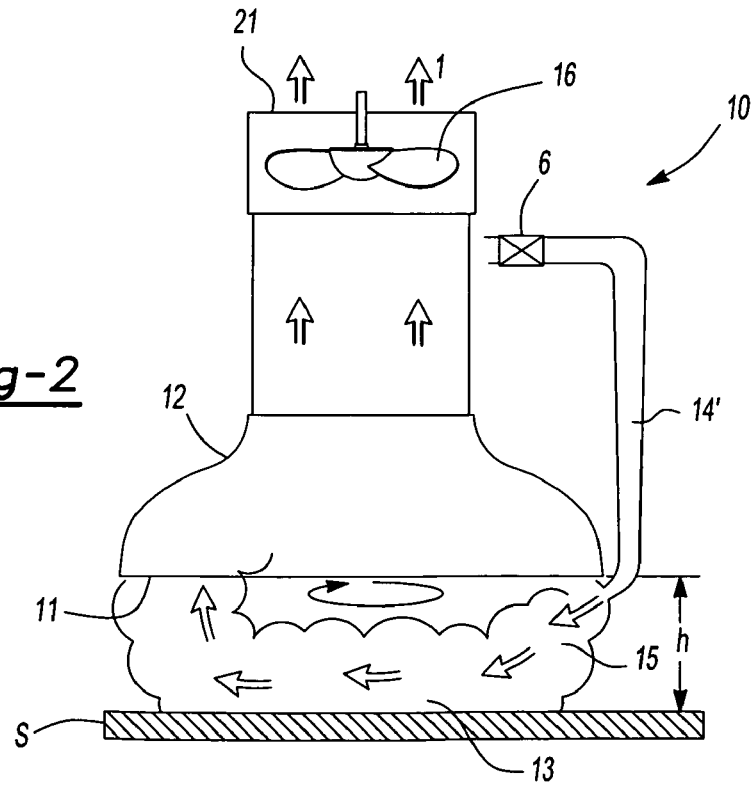
FIG. 2 is a side view of a second embodiment of an aerodynamic sampler according to the present invention.

Turning now to FIG. 1, a first embodiment of an aerodynamic sampler 10 according to the present invention is shown. This embodiment may be referred to as a jet-puff sniffer, the sniffer 10 including an outer, properly-shaped, duct or shroud 12 and an outlet nozzle 14 disposed inside the shroud. In the alternative, a second embodiment wherein an outlet nozzle 14' is disposed outside the shroud 12 is shown in FIG. 2. Furthermore, it is appreciated that the nozzle 14 shown in FIG. 1 is positioned along a central axis of the shroud 12, however this is not required.

A source of compressed gas 18, illustratively including compressed air, nitrogen, argon, oxygen and the like, is connected to the outlet nozzle 14 to provide a jet 19, namely a pulse of gas, to a sampling surface S. In some instances, the jet 19 has a pressure up to 10 atmospheres. In other instances, the jet 19 has a pressure of between 1 and 10 atmospheres, while in still yet other instances the jet 19 has a pressure between 2 and 8 atmospheres. A standoff distance h defined as the distance from the shroud 12 to the sampling surface S is preferably small, typically comparable to or preferably less than the shroud diameter, for successful operation. In the alternative, the sampler 10 can be placed in a moving stream and used to sample a moving airstream and the like.

A suction device 16 in the form of a fan, blower or the like draws a sample flow into the shroud 12 through a first opening, also known as a shroud inlet 11, and through a second opening, also known as a shroud outlet 21, as indicated by arrows 1. It is appreciated that the sample flow or a portion thereof can be delivered to a detector for analysis, for example to optional chemical analyzer 100, or to a pre-concentrator if so required. It is further appreciated that the jet 19 can be provided by a source of compressed gas, modern synthetic jet technology [11] or the like, the jet 19 providing an axisymmetric wall jet 13 that separates from the sample surface S as shown in FIG. 1 due to the adverse pressure gradient imposed upon sample surface S by the shroud inlet 12 and associated airflow. In the alternative, a non-axisymmetric wall jet 13' that also separates from the sample surface S is shown in FIG. 2. It is appreciated that the shroud 12 along with the outlet nozzle 14 and 14' are directed generally in the same direction, which in this case is toward the sampling surface S.

The supply of compressed gas to the nozzle 14 and 14' can be controlled by solenoid valves known to those skilled in the art and can range from intermittent duration of a few milliseconds to continuous operation. In order to scour a surface and remove particles and/or vapor, a shear stress in the range of 10-30 Pascals (Pa) (0.0015-0.0045 pounds per square inch (psi)) can be used. For example, and for illustrative purposes only, an outlet nozzle having an exit opening with an inside diameter of 1 millimeter (mm) (0.04 inch (in.)) with a standoff distance of 25 mm (1 in.) and a nozzle-exit stagnation pressure of 14 kPa (2 psi) above atmospheric pressure can provide such a shear stress. Such a pressure would result in a mass flow rate through the nozzle of 0.00015 kilograms per sec (kg/sec), corresponding to a volume flow rate of $1.17 \times 10^{-4}$ cubic meters per second ($m^3$/sec) (0.25 standard cubic feet per minute (SCFM)). Taking for example a shroud that can collect 5 to 10 times the volume flow rate of the outlet nozzle, i.e. $5.85 \times 10^{-4}$-$1.17 \times 10^{-3}$ $m^3$/sec (1.25-2.5 SCFM), a diameter of such a shroud could be of the order of 12 centimeters (cm) (4.7 in.). Larger diameter outlet nozzles could naturally result in higher mass flow rates out of the nozzle and thus larger shrouds. Smaller devices may likewise be designed.

Figure 3:
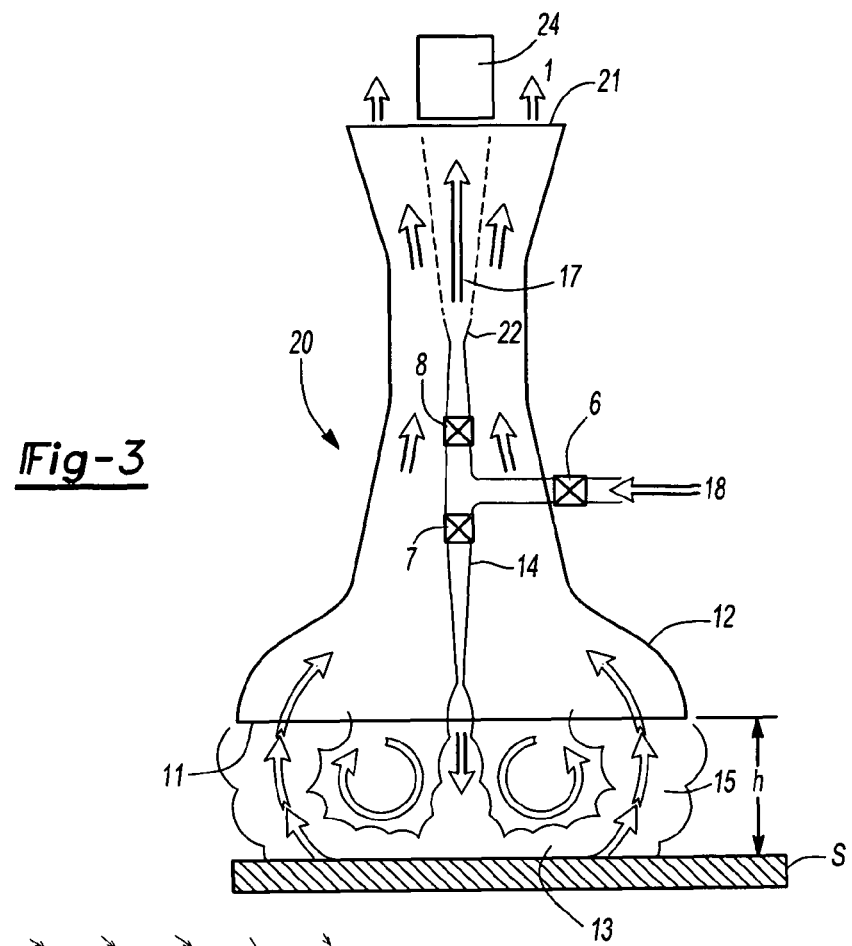
FIG. 3 is a side view of a third embodiment of an aerodynamic sampler according to the present invention.

In an alternate embodiment shown in FIG. 3, where like numerals represent like elements as referenced in previous figures, a sniffer 20 includes an ejector nozzle 22 directed away from the shroud inlet 11 and towards the shroud outlet 21. The compressed-air source 18 can simultaneously power the jet 19 and provide a suction using the ejector 22 which induces a low-speed flow by way of a pressure drop created by entrainment into a small high-speed turbulent jet 17. A dumptube 24 may be provided proximate the shroud outlet 21 in order to collect jet 17 and discard it, thus increasing the concentration of a trace signal originating from the surface S and presented to a detector (not shown) via the airflow indicated by arrows 1. In addition, optional valves 6, 7 and 8, can be included and used to direct compressed gas to the outlet nozzle 14 and/or ejector 22. It is appreciated that the embodiment illustrated in FIG. 3 can be modified in a similar fashion as the embodiment shown in FIG. 2 with an outlet nozzle 14' disposed outside the shroud 12, or in a different non-axially-symmetric form.

As noted in earlier discussion, the "reach" of heretofore inlets is quite limited. The flow into a bulbous-shaped shroud (i.e., shaped like an animal nose) could be focused in a forward direction to improve the "reach" of sniffing if inlet walls were able to generate vorticity aimed towards a central suction opening. One method to generate such vorticity aimed towards the central suction opening is with moving walls. However, this method requires great mechanical complexity. In the alternative, the same effect can be accomplished with a Coanda-inlet sampler 30 shown schematically in FIG. 4. It is appreciated that Henri Coanda proposed [5] an explanation of why a fluid flow clings to a curved surface. Various inventions have put this principle to use, for example in kitchen ventilation [6], but not thus far to the type of aerodynamic sampling described in the present disclosure.

The sampler 30 includes a shroud 32 with an outer portion 34 and an inner portion 36. An outward "step" nozzle 38 is disposed between the outer portion 34 and the inner portion 36 and can be formed by a gap 39 therebetween. It is appreciated that the shroud 32 and/or step nozzle 38 can be axisymmetric in orientation and/or position, or in the alternative, not be axisymmetric. Attached surface jets 35, generated by compressed gas 37 flowing through the step nozzle 38 and aimed inward, entrain air in order to "focus" the flow. The sampler 30 functions in some sense similarly to the ejector 22 shown in FIG. 3 and a capture or sample tube 40 captures only the incoming airstream 42 from the immediate forward direction. The remaining air flux can be discarded, in that it does not arise from the desired forward direction and is thus irrelevant to the desired sampling task.

Figure 4:
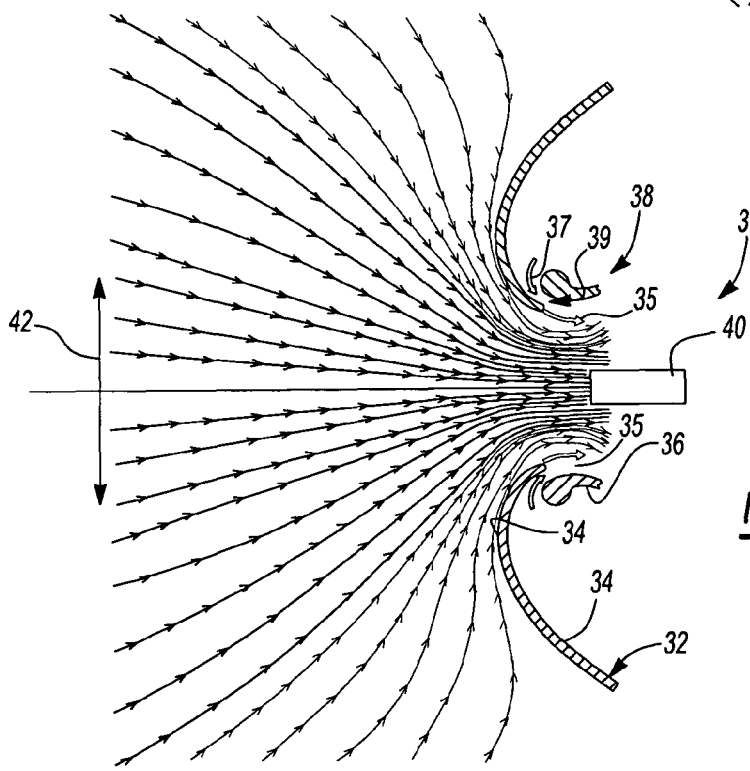
FIG. 4 is a side view of a fourth embodiment of an aerodynamic sampler according to the present invention.
Figure 5:
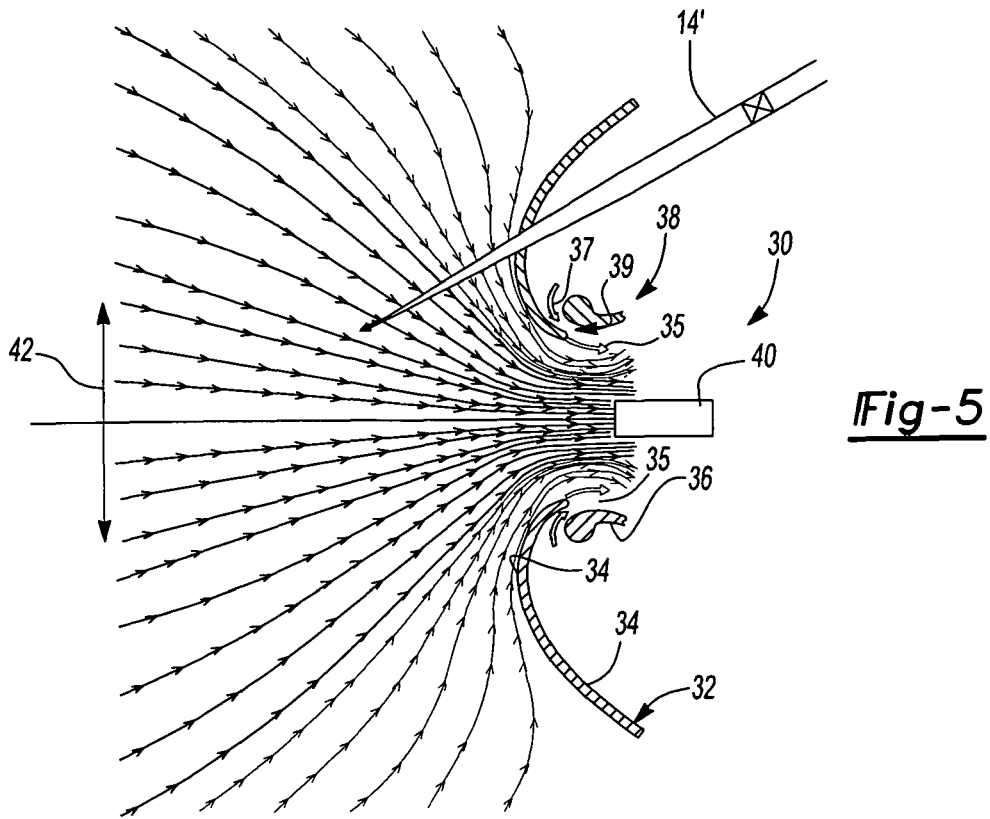
FIG. 5 is a side view of a fifth embodiment of an aerodynamic sampler according to the present invention.

It is appreciated that the location of the step nozzle 38 in FIG. 4 is for illustrative purposes only and in no way limits the embodiment. An inlet of this type typically requires compressed gas to power the Coanda jets 35. A suction can be applied to the capture tube 40 in order to extract the sampled air and subsequently present it to a detector. The sampler 30 may be used in conjunction with puffer jets, described earlier, in order to dislodge particles and/or vapor from surfaces before "sniffing" them. It is further appreciated that the sample tube 40 can provide the puffer jet, or in the alternative, an outlet nozzle 14' as shown in FIG. 5 can be provided to afford for a jet of compressed gas to impact a sample surface.

For example, and in no way limiting the scope of the embodiment, the sampler 30 could have an inside diameter of shroud 36 of 51 mm (2 inches (in)) with a sample tube 40 having an inside diameter of 13 mm (0.5 inch). Thus in operation, a centrifugal blower known to those in the art could supply the Coanda jet flow 37 with a volume flow rate of 0.014 m³/sec (30 SCFM) that would be drawn into the sampler 30 through the inside diameter of shroud 36. Such a volume flow rate would produce a velocity of 7 meters per second (m/sec) and the sample tube 40 could draw in a volume flow rate of $9.4 \times 10^{-4}$ m³/sec (2 SCFM). It is appreciated that the gas flow could be drawn from a region 42 that can be of similar diameter as the inside diameter of the shroud 36 and located as much as, or more than one diameter away from the sampler 30.

Figure 6:
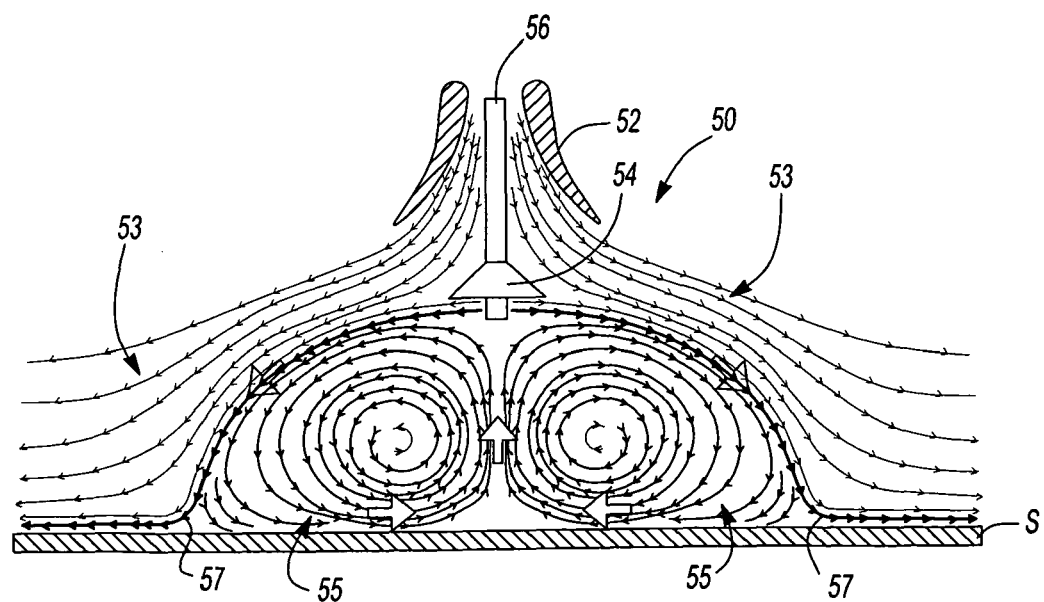
FIG. 6 is a side view of a sixth embodiment of an aerodynamic sampler according to the present invention.
Figure 7:
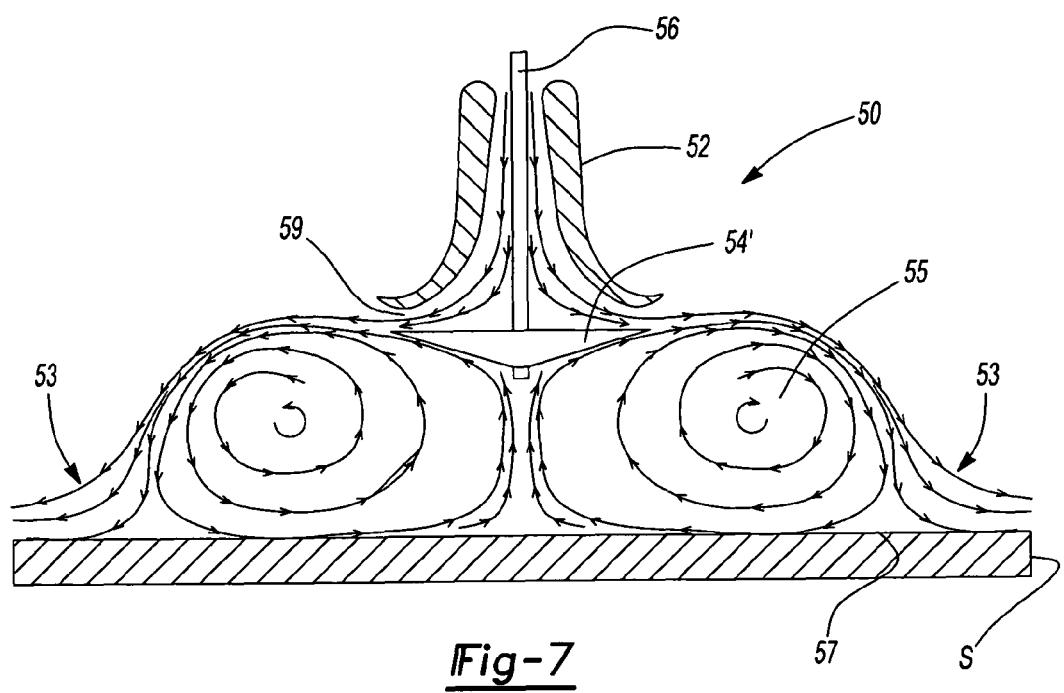
FIG. 7 is a side view of a seventh embodiment of an aerodynamic sampler according to the present invention.

Another embodiment of a sampler or sniffer according to the present invention is shown generally at reference numeral 50 in FIGS. 6 and 7. This design may be referred to as a radial-jet reattachment sniffer, and works in a manner logically opposite to that of the jet-puff sniffer taught above in that radial jet 53 is produced from a nozzle 52 combined with a flare 54 or 54'. Near a surface S, the radial jet 53 attaches to the surface S and produces an internal toroidal vortex 55 between the nozzle flare 54 and the surface S. The vortex 55 sweeps air across the surface S, inward radially from a jet reattachment line 57, and upward along a centerline where a sample tube 56 withdraws some of the trace-laden air for the chemical detection step.

It is appreciated that if the nozzle shroud 52 and flare 54 are angled sharply downward toward the surface S as shown in FIG. 6, then a local surface area of small diameter is sampled. In the alternative, the nozzle flare 54' and corresponding radial slot angle 59 can be parallel to the sampling surface S or even inclined up to 30 degrees away from it, and thereby result in a larger-sized radial jet reattachment circular "footprint" on the surface S, as shown in FIG. 7. As such, the embodiment affords for large semi-flat surfaces to be sampled, such as suitcases, the door panels of automobiles, etc. It is further appreciated that the samplers resulting in the flow patterns shown in FIGS. 6 and 7 can be made to be simply interchangeable on the front-end of a trace chemical detection system and/or that many different designs of the nozzle-flare combination 52-54, 52-54' and the like are possible with approximately the airflow effect shown in these figures afforded. In this manner, the sampling surface area for a trace chemical detection system can be varied and thereby provide a single detection system with multiple interchangeable samplers that afford for different-sized surfaces to be tested.

Figure 8:
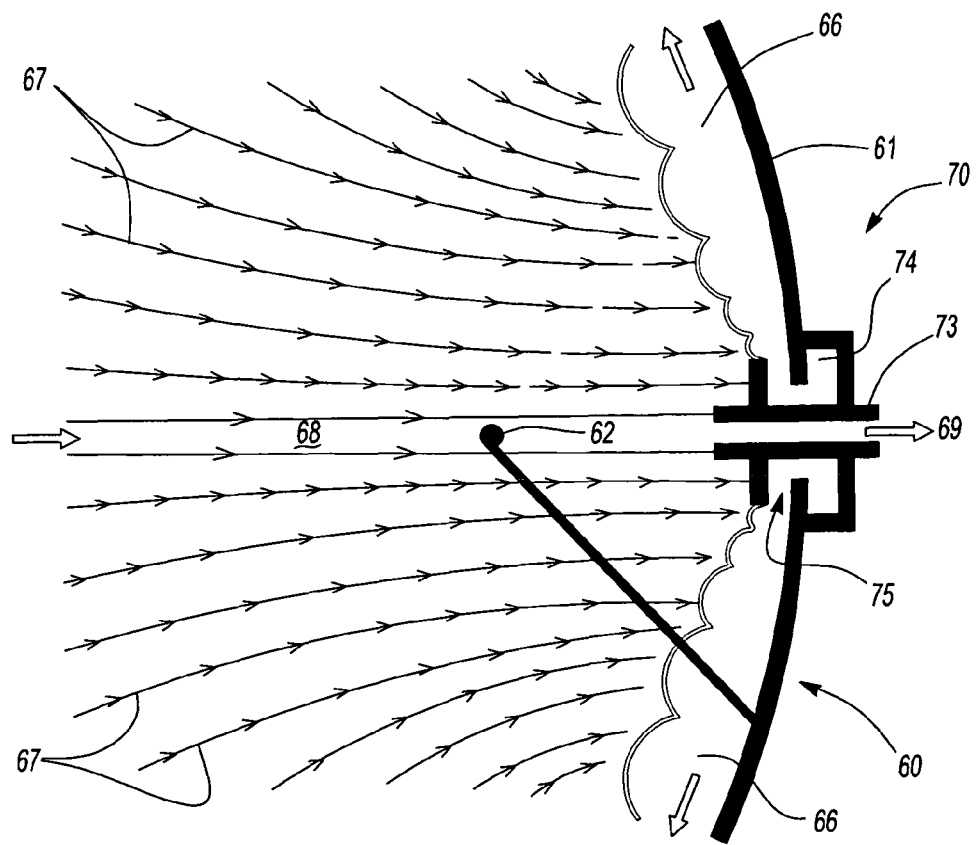
FIG. 8 is a side view of an eighth embodiment of an aerodynamic sampler according to the present invention.

Another embodiment of a sampler or sniffer is shown in FIG. 8 wherein an aerodynamically-assisted sniffer 70 may be integrated with a parabolic "dish" antenna 60. Vehicles and robotic devices often incorporate parabolic dish antennas for communications and/or for electromagnetic interrogation of a target. Sophisticated actuators are required to aim the dish antenna for these purposes. The same equipment may serve the dual purpose of directional "sniffing" in close proximity to objects, given the antenna modifications illustrated in FIG. 8. The electromagnetically-active components of the antenna 60 are the parabolic reflector dish 61 and a signal "pickup" stalk 62 positioned at a parabola focus of the dish 61.

Figure 9:
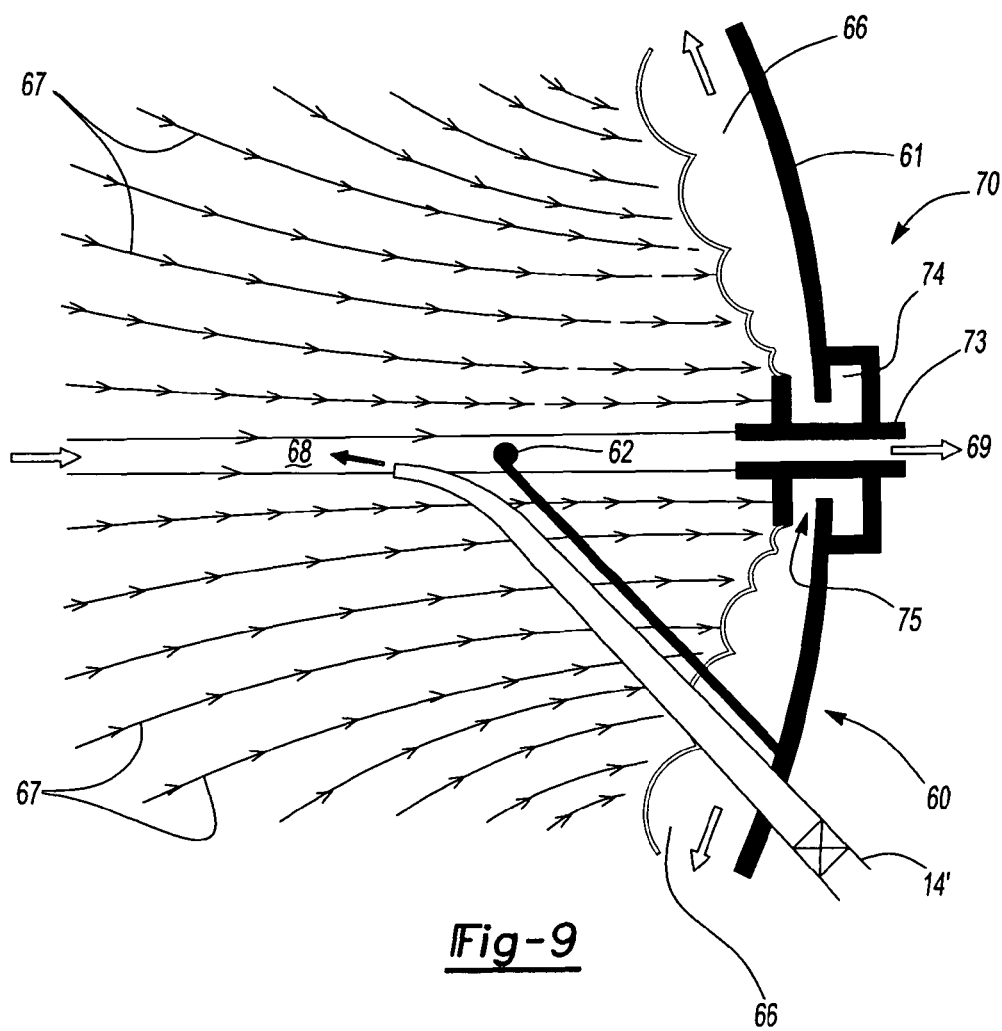
FIG. 9 is a side view of a ninth embodiment of an aerodynamic sampler according to the present invention.

The sniffer 70 includes a sampling tube 73, plenum 74 and radial nozzle 75 as shown in FIG. 8. In addition, compressed air from plenum 74 can be used to generate a radially-outward-flowing turbulent boundary layer 66 along an inner surface of the parabolic reflector dish 61 and thereby afford by entrainment a bulk airflow motion indicated by streamlines 67. In the alternative, an optional outlet nozzle 14' can be provided as shown in FIG. 9, the outlet nozzle 14' affording for compressed gas to impact a sample surface as taught above. In this manner, a narrow stream-tube 68 may be sampled from a direction in which the dish antenna 60 is aimed, and may thus provide a small directional airflow 69 to a chemical detector mounted aft of the antenna 60 and not shown in FIGS. 8 and 9.

Thus, with the modifications described above, a parabolic dish antenna can also serve a second purpose of directional sniffing for the aerodynamic interrogation of a suspected explosive device, an automobile, a person, etc. for trace chemical species. In FIGS. 8 and 9 the electromagnetic pickup on the stalk 62 may produce some interference with the aerodynamic sampling function of stream 68, but such interference can be negligible. Stated differently, any interference of the antenna's electromagnetic function by the airflow is likewise appreciated to be negligible. In some instances, compressed air is first ejected through sampling tube 73 in a direction towards the stalk 62 and produces a turbulent jet that can impinge upon a surface to be sampled (to the left in FIGS. 8 and 9, not shown) and dislodge particles and/or vapor via induced surface shear stress. After a brief interval, suction through sampling tube 73, discussed above and shown in FIGS. 8 and 9, can "inhale" particles and/or vapor from a sample surface and thence present them to a detection device.

Such a parabolic dish antenna 61 for a mobile electromagnetic communication device could have a diameter of 46 cm (18 in.) with a collection tube 73 having an inner diameter of 2.5 cm (1 in.) and a slot nozzle 75 having a width of 5 mm (0.2 in.) and a circumference of 23 cm (9 in.). Such dimensions would allow for a gas flow rate of 0.36 m³/sec (77 SCFM) out of the slot nozzle 75 and a suction flow of 0.005 m³/sec (11 SCFM) through the capture tube 73, thereby affording for a "reach" of the captured stream-tube 68 to extend from the end of the capture tube 73 to a distance ahead of the parabolic dish antenna 61 equal to, if not greater than the diameter of the dish antenna 61.

As will be clear to those of skill in the art, the embodiments of the present invention described and illustrated herein may be altered in various ways without departing from the scope or teaching of the present invention. For example, all of the embodiments can be used to sample a moving airstream as well as a surface and heated air can be used in the puffer jets in order to better desorb volatile chemicals from a surface. As such, the invention is not restricted to the illustrative examples and/or embodiments described above and the scope of the invention is defined by the scope of the claims.

REFERENCES

The following are incorporated herein in their entirety by reference:

[1] Settles, G. S., "Sniffers—Fluid-dynamic sampling for olfactory trace detection in nature and Homeland Security," *J. Fluids Engrg.* Vol. 127, No. 2, pp. 189-218, March 2005.
[2] Goodfellow H, Tähti E, eds. (2001) Local ventilation. Ch. 10 of *Industrial Ventilation Design Guidebook*. Academic Press, NY.
[3] H. W. Shin, W. K. Cheng, E. M. Greitzer, and C. S. Tan. Inlet vortex formation due to ambient vorticity intensification. *AIAA Journal* 24 (4):687-689, 1986.
[4] US Patent Application Publication No. 2003/0155506 by V. S. Motchkine, L. Y. Krasnobaev, and S. N. Bunker; U.S. Pat. No. 6,828,795 by L. Y. Krasnobaev, V. S. Persenkov, V. V. Belyakov, V. B. Kekukh, S. N. Bunker; U.S. Pat. No. 6,861,646 by V. S. Motchkine, L. Y. Krasnobaev, and S. N. Bunker.
[5] U.S. Pat. No. 2,052,869 by H. Coanda.

[6] Roehl-Hager, H., Koppenwallner, G., and Koppenwallner, G. E., German Patent DE 196 13 513.3, 1996.
[7] R. H. Page, L. L. Hadden, and C. Ostowari. Theory for radial jet reattachment flow. *AIAA Journal* 27 (11):1500-1505, 1989.
[8] Smedley G T, Phares D J, Flagan R C (1999) Entrainment of fine particles from surfaces by gas jets impinging at normal incidence. *Experiments in Fluids* 26, 324-334.
[9] Gary S. Settles, Heather C. Ferree, Michael D. Tronosky, and Zachary M. Moyer, and William J. McGann, "Natural Aerodynamic Portal Sampling of Trace Explosives from the Human Body," FAA 3$^{rd}$ International Symposium on Explosive Detection and Aviation Security, Nov. 26-30, 2001, Atlantic City, N.J.
[10] H. Z. Lai, J. W. Naughton, and W. R. Lindberg. An experimental investigation of starting impinging jets. *Journal of Fluids Engineering* 125 (2):275-282, 2003.
[11] Smith B L, Glazer A, "Formation and Evolution of Synthetic Jets" Physics of Fluids, vol. 10, pp 2281-2297, 1988.
[12] U.S. Pat. No. 6,171,656 by G. S. Settles.
[13] U.S. Pat. No. 4,043,257 by C. P. N. Aaberg; U.S. Pat. No. 4,909,090 by J. B. McGown, E. E. A. Bromberg and L. W. Noble; U.S. Pat. No. 5,092,157 by E. K. Achter, A. L. Carroll, D. P. Rounbehler, D. H. Fine and F. W. Fraim; U.S. Pat. No. 5,123,274 by R. C. Smith; U.S. Pat. No. 5,376,550 by D. H. Fine, F. W. Fraim, S. J. MacDonald and K. M. Thrash, Jr.; U.S. Pat. No. 6,269,703 by W. D. Bowers.

I claim:

1. An aerodynamic sampler for sampling particles from a surface, the aerodynamic sampler comprising:
   an arcuate-shaped shroud having a first opening and a second opening, said first opening being directed in a first direction and said second opening oppositely disposed and spaced apart from said first opening;
   a gas nozzle having at least one gas outlet, said gas outlet being directed generally in the first direction;
   a suction device operable to cause gas to flow in through said first opening, through said arcuate-shaped shroud and out through said second opening; and
   a Coanda jet surrounding said gas nozzle and operable as said suction device.

2. The sampler of claim 1, wherein said arcuate-shaped shroud is a bell-shaped shroud with said first opening located at a bottom of said bell-shaped shroud.

3. The sampler of claim 1, wherein said gas nozzle is at least partially within said bell-shaped shroud.

4. The sampler of claim 1, wherein said arcuate-shaped shroud is a splayed-shaped shroud with said first opening located at a wide end of said splayed-shaped shroud.

5. The sampler of claim 4, further comprising a flare proximate said first opening, said flare operable to spread a gas flow exiting said gas nozzle and directed in the first direction.

6. The sampler of claim 5, further comprising a sampling tube extending beyond said flare in the first direction, said sampling tube in fluid connection with said suction device.

7. The sampler of claim 1, wherein said arcuate-shaped shroud is a parabolic-shaped shroud with said first opening located at a wide end of said parabolic-shaped shroud.

8. The sampler of claim 7, further comprising a plenum proximate said second opening, said plenum in fluid communication with said gas nozzle and operable to generate a radial turbulent boundary layer along an inner surface of said parabolic-shaped shroud.

9. The sampler of claim 7, further comprising a sampling tube extending beyond said second end in the first direction, said sampling tube in fluid connection with said suction device.

10. An aerodynamic sampler for sampling particles from a surface, the aerodynamic sampler comprising:
    a parabolic-shaped shroud having a first opening and a second opening, said first opening being directed in a first direction and located at a wide end of said parabolic-shaped shroud, said second opening oppositely disposed and spaced apart from said first opening;
    a gas nozzle having at least one gas outlet, said gas outlet being directed generally in the first direction;
    a suction device operable to cause gas to flow in through said first opening, through said parabolic-shaped shroud and out through said second opening; and
    a plenum proximate said second opening, said plenum in fluid communication with said gas nozzle and operable to generate a radial turbulent boundary layer along an inner surface of said parabolic-shaped shroud.

11. The sampler of claim 10, wherein said first opening is located at a bottom of said parabolic-shaped shroud.

12. The sampler of claim 10, wherein said gas nozzle is at least partially within said parabolic-shaped shroud.

* * * * *